United States Patent
Akmal et al.

(10) Patent No.: US 11,833,445 B2
(45) Date of Patent: Dec. 5, 2023

(54) METHOD AND DEVICE FOR SEPARATING AND MEASURING MULTIPHASE IMMISCIBLE FLUID MIXTURES USING AN IMPROVED ANALYTICAL CELL

(71) Applicant: SAUDI ARABIAN OIL COMPANY, Dhahran (SA)

(72) Inventors: Naim Akmal, Dhahran (SA); Said Shahrani, Dhahran (SA); Saleh Sharidi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/482,169

(22) Filed: Sep. 22, 2021

(65) Prior Publication Data
US 2023/0089200 A1 Mar. 23, 2023

(51) Int. Cl.
*B01D 17/06* (2006.01)
*B01D 17/02* (2006.01)
(Continued)

(52) U.S. Cl.
CPC ......... *B01D 17/0205* (2013.01); *B01D 17/06* (2013.01); *E21B 49/08* (2013.01); *G01N 27/10* (2013.01)

(58) Field of Classification Search
CPC .... B01D 17/0205; B01D 17/02; B01D 17/06; B01D 17/12; B01D 17/047; E21B 49/08; G01N 27/10
See application file for complete search history.

(56) References Cited

U.S. PATENT DOCUMENTS

| 3,712,118 A | 1/1973 | Mason et al. |
| 4,481,130 A | 11/1984 | Robertson |

(Continued)

FOREIGN PATENT DOCUMENTS

| CN | 101670197 B | 12/2011 |
| CN | 102128658 B | 7/2012 |

(Continued)

OTHER PUBLICATIONS

Rodriguez et al., "Treatment of Produced Water in the Permian Basin for Hydraulic Fracturing: Comparison of Different Coagulation Processes and Innovative Filter Media", MDPI Water, 12, 770, Mar. 11, 2020, pp. 1-16.

(Continued)

*Primary Examiner* — Tarun Sinha
*Assistant Examiner* — James I Burris
(74) *Attorney, Agent, or Firm* — Bracewell LLP; Constance G. Rhebergen; Keith R. Derrington (57) ABSTRACT

Methods and devices for obtaining approximate property data from the aqueous liquid phase of a multiphase fluid produced from a well. The device includes a separation vessel; a demulsifier source; a fresh water source configured to dilute an aqueous liquid phase sample; a water analysis unit configured to receive and analyze the diluted aqueous liquid phase sample, the water analysis unit comprising an analytical cell and at least one probe, the at least one probe having a membrane-coated sensor tip wherein the membrane-coated sensor tip having a membrane coating that comprises a polar material, the at least one probe being configured to measure a property of the diluted aqueous liquid phase sample to obtain diluted aqueous liquid phase sample data; a processing unit configured to calculate approximate aqueous liquid phase data accounting for the (Continued)

measured amount of fresh water used to dilute the measured sample of the aqueous liquid phase.

19 Claims, 2 Drawing Sheets

(51) Int. Cl.
*E21B 49/08* (2006.01)
*G01N 27/10* (2006.01)

(56) References Cited

U.S. PATENT DOCUMENTS

| | | | |
|---|---|---|---|
| 4,581,134 | A | 4/1986 | Richter, Jr. et al. |
| 5,078,856 | A | 1/1992 | Yamaguchi et al. |
| 5,637,201 | A | 6/1997 | Raguse et al. |
| 5,741,409 | A | 4/1998 | Raguse et al. |
| 5,753,093 | A | 5/1998 | Raguse et al. |
| 6,004,442 | A | 12/1999 | Choulga et al. |
| 6,872,239 | B2 | 3/2005 | Nilsen et al. |
| 7,140,441 | B2 | 11/2006 | Hauge et al. |
| 7,147,788 | B2 | 12/2006 | Tveiten |
| 7,231,819 | B2 | 6/2007 | Jones et al. |
| 7,373,813 | B2 | 5/2008 | DiFoggio |
| 7,474,969 | B2 | 1/2009 | Poulisse |
| 7,661,302 | B2 | 2/2010 | Gysling |
| 7,775,085 | B2 | 8/2010 | Scott |
| 7,966,892 | B1 | 6/2011 | Halilah |
| 8,177,958 | B2 | 5/2012 | Lawrence et al. |
| 8,720,573 | B2 | 5/2014 | Eriksen |
| 8,790,509 | B2 | 7/2014 | Vu |
| 8,935,100 | B2 | 1/2015 | Weiner et al. |
| 9,052,285 | B2 | 6/2015 | Muller et al. |
| 9,239,406 | B2 | 1/2016 | Kalia et al. |
| 9,284,705 | B2 | 3/2016 | Theegala |
| 9,314,715 | B2 | 4/2016 | Grave et al. |
| 9,341,058 | B2 | 5/2016 | Keizer et al. |
| 9,540,574 | B2 | 1/2017 | Janssen et al. |
| 9,658,178 | B2 | 5/2017 | Surman et al. |
| 9,696,193 | B2 | 7/2017 | Martin et al. |
| 9,840,895 | B1 * | 12/2017 | Kuhn ..................... E21B 43/12 |
| 9,863,926 | B2 | 1/2018 | Kriel et al. |
| 10,023,811 | B2 | 7/2018 | Soliman et al. |
| 10,260,010 | B2 | 4/2019 | Soliman |
| 10,350,515 | B2 | 7/2019 | Al-Shafei et al. |
| 10,597,313 | B2 | 3/2020 | Raynel et al. |
| 2012/0111571 | A1 | 5/2012 | Eriksen |
| 2013/0026082 | A1 * | 1/2013 | Al-Shafei ............... C10G 31/08 210/96.1 |
| 2016/0052799 | A1 * | 2/2016 | Grave ...................... C02F 1/38 210/97 |
| 2017/0319984 | A1 * | 11/2017 | Oshinowo ............... B01D 21/30 |
| 2018/0244539 | A1 | 8/2018 | Asdahl et al. |
| 2018/0299423 | A1 | 10/2018 | Leblanc |
| 2019/0010796 | A1 | 1/2019 | De Freitas et al. |
| 2019/0049425 | A1 | 2/2019 | Marshall et al. |
| 2019/0211274 | A1 | 7/2019 | Soliman et al. |
| 2020/0102234 | A1 | 4/2020 | Patton |
| 2020/0255748 | A1 * | 8/2020 | Soliman ................. C10G 32/02 |
| 2021/0102831 | A1 | 4/2021 | Ahmad et al. |
| 2022/0380688 | A1 | 12/2022 | Soliman |
| 2023/0086247 | A1 | 3/2023 | Akmal et al. |
| 2023/0089200 | A1 | 3/2023 | Akmal et al. |
| 2023/0093403 | A1 | 3/2023 | Akmal et al. |

FOREIGN PATENT DOCUMENTS

| | | |
|---|---|---|
| NO | 2001074468 A3 | 10/2001 |
| WO | 2021043923 A1 | 3/2021 |

OTHER PUBLICATIONS

Ghorbani et al., "Validating Automated Real-Time Produced Water Composition Measurement Device With Field Produced Water Samples: A Pathway to Filed Trial", SPE-188244-MS, Nov. 13, 2017, 2 pages.

Hach, "Complete Water Analysis for the Upstream Oil & Gas Industry", 2014, 20 pages.

Hansen et al., "Multi-Phase Flow Metering in Offshore Oil and Gas Transportation Pipelines: Trends and Perspectives", WWW.mdpi.com/journal/sensors, 19, 2184, May 11, 2019, pp. 1-26.

Roach et al., "A Multiphase Flow Meter for the On-Line Determination of the Flow Rates of Oil, Water and Gas", AU9817323, 1997, CSIRO Minerals, pp. 106-111.

Andreussi, P. et al.; "Application of a wet gas meter to detect extremely low liquid volume fractions" BHR Group 2007 Multiphase Production Technology 13; pp. 297-308.

* cited by examiner

METHOD AND DEVICE FOR SEPARATING AND MEASURING MULTIPHASE IMMISCIBLE FLUID MIXTURES USING AN IMPROVED ANALYTICAL CELL

BACKGROUND OF THE INVENTION

1. Technical Field

The disclosure relates to methods and apparatuses of separating and measuring multiphase fluid mixtures; particularly mixtures produced from hydrocarbon-bearing formations.

2. Discussion of Related Art

Fluids produced from hydrocarbon-bearing formations typically vary in their composition over time. Generally a greater amount of crude oil is produced initially. However, over time the amount of produced water increases and the amount of crude oil produced decreases. It is necessary to know the amount of crude oil and produced water produced from a given well in order to manage the well and oil field.

Conventionally, the amount of crude oil produced from a well is measured by analyzing samples of fluids produced from the well in a laboratory. Typically, a sample of a fluid is collected, the crude oil is allowed to separate from produced water in the sample, and a sample of the produced water is taken to a secondary filtration or separation unit where it is treated to remove any residual oil. A portion of the produced water is then analyzed in a laboratory to measure certain geophysical properties. The data obtained by this analysis is used to calibrate a multiphase flow meter.

SUMMARY OF THE INVENTION

Disclosed are processes and devices for separating and analyzing a multiphase fluid. The processes and devices allow for automated continuous analysis of discrete samples of a multiphase fluid, and can provide reliable and timely data for calibrating, optimizing, and controlling a multiphase flow meter.

A device for separating and analyzing an aqueous liquid phase from a multiphase fluid produced from a hydrocarbon-bearing formation is described. The device includes: a separation vessel having a first inner chamber defined in the separation vessel for containing a discrete sample of the multiphase fluid. The separation vessel includes a multiphase fluid inlet to allow the discrete sample of the multiphase fluid to flow into the first inner chamber of the separation vessel, and an aqueous liquid phase outlet that is configured to draw a measured sample of an aqueous liquid phase from within the inner chamber to be carried by an aqueous liquid phase stream, which conducts the sample of the aqueous liquid phase to a water analysis unit. The device also includes a demulsifier source in fluid communication with the separation vessel and configured to introduce a demulsifier to the first inner chamber of the separation vessel, and a fresh water source that is in fluid communication with the aqueous liquid phase stream and that is configured to introduce a measured amount of fresh water to the measured sample of the aqueous liquid phase to obtain a diluted aqueous liquid phase sample. The water analysis unit includes an analytical cell having a second inner chamber and at least one probe, and is configured to receive the diluted aqueous liquid phase sample and analyze it. The at least one probe can have a membrane-coated sensor tip having a membrane coating that includes a polar material, and can be configured to measure a property of the diluted aqueous liquid phase sample to obtain diluted aqueous liquid phase sample data. The device can also include a processing unit that is configured to receive the diluted aqueous liquid phase sample data and calculate an approximate aqueous liquid phase data by accounting for the measured amount of fresh water used to dilute the measured sample of the aqueous liquid phase.

According to at least one embodiment, the at least one probe is configured to measure a property selected from the group consisting of total dissolved solids (TDS), salinity, pH, conductivity, sodium concentration, chloride, concentration, sulfate concentration, carbonate concentration, nitrate concentration, and any combination of the same. According to at least one embodiment, the at least one probe can include an ion-selective electrode. According to at least one embodiment, the at least one probe can be oriented in a fixed position in the second inner chamber with the membrane-coated sensor tip in a downward direction so that the angle measured from the at least one probe to a horizontal plane (i.e., orthogonal to the direction of gravity) can be acute (e.g., between 10 and 80 degrees).

According to at least one embodiment, the membrane coating on the sensor tip can include a material selected from the group consisting of polyvinyl acetate, polyimide, polybenzimidazole, polyacrylonitrile, polyethersulfone, and combinations of the same.

According to at least one embodiment, the second inner chamber of the analytical cell defines a space having a shape that funnels liquid toward an outlet.

According to at least one embodiment, the processing unit can be configured to calculate the approximate aqueous liquid phase data by accounting for the measured amount of fresh water used to dilute the measured sample of the aqueous liquid phase and a corresponding property of the fresh water.

According to at least one embodiment, the analytical cell includes a closed loop controller for emptying and filling the analytical cell.

According to at least one embodiment, the device can also include a control box configured to receive a reading from the at least one probe, convert the reading to the diluted aqueous liquid phase data in a digital form, and electronically send the diluted aqueous liquid phase data to the processing unit.

A method is described for obtaining an approximate aqueous liquid phase property data from a multiphase fluid that is produced from a hydrocarbon-bearing formation and using the approximate aqueous liquid phase property data to calibrate a multiphase flow meter. The method includes the steps of: introducing a discrete sample of the multiphase fluid to a separation vessel; introducing and mixing a demulsifier with the discrete sample of the multiphase fluid in the separation vessel; allowing the multiphase fluid to separate for a first period of time into separate liquid phases comprising an aqueous liquid phase and a nonpolar liquid phase; drawing a measured sample of the aqueous liquid phase from the separation vessel, and diluting it with a measured amount of fresh water to obtain a diluted aqueous liquid phase sample; analyzing the diluted aqueous liquid phase sample in a water analysis unit to measure a property of the diluted aqueous liquid phase sample and obtain diluted aqueous liquid phase sample data by introducing the diluted aqueous liquid phase sample to an analytical cell having at least one probe configured to measure a property of the diluted aqueous liquid phase sample, allowing the diluted aqueous liquid phase sample to remain in contact with the at least one probe for a second period of time, using the at least one probe to observe the property and obtain the diluted aqueous liquid phase sample data; calculating the approximate aqueous liquid phase property data by adjusting the diluted aqueous liquid phase sample data to account for the measured amount of fresh water used to dilute the measured sample of the aqueous liquid phase; and using the approximate aqueous liquid phase property to calibrate the multiphase flow meter.

According to at least one embodiment, the property of the diluted aqueous liquid phase sample can be selected from the group consisting of TDS, salinity, pH, conductivity, sodium concentration, chloride concentration, sulfate concentration, carbonate concentration, nitrate concentration, and any combination of the same.

According to at least one embodiment, the step of analyzing the diluted aqueous liquid phase sample in a water analysis unit can be carried out using a probe that includes an ion-selective electrode.

According to at least one embodiment, the first period of time can be between 20 minutes and 24 hours. According to at least one embodiment, the second period of time can be between 30 seconds and 1 hour.

According to at least one embodiment, the method also includes flushing the analytical cell with fresh water after measuring the diluted aqueous liquid phase sample. According to at least one embodiment, the method also includes emptying the water analysis unit and the first inner chamber of the separation vessel and repeating the steps off the method continuously. According to another embodiment, the steps can be carried out over a third period of time that can be between 5 minutes and 6 hours.

BRIEF DESCRIPTION OF THE DRAWING

The embodiments disclosed will be understood by the following detailed description along with the accompanying drawing. The embodiments shown in the figure only illustrate several embodiments of the disclosure. The disclosure admits of other embodiments not shown in the figure, and is not limited to the content of the illustrations. Similar streams, units, or features may have similar reference labels in the drawings.

DETAILED DESCRIPTION OF THE DRAWING

For certain embodiments, many details are provided for thorough understanding of the various components or steps. In other instances, known processes, devices, compositions, and systems are not described in particular detail so that the embodiments are not obscured by detail. Likewise, illustrations of the various embodiments can omit certain features or details so that the various embodiments are not obscured. In the figures, fluid streams can be represented by lines. A person of ordinary skill will understand that fluid streams can be conveyed by various means, including but not limited to pipes, conduit, channels, and their attachments and fittings. Though other equipment, such as pumps, valves, storage tanks, reflux drums, reflux streams, controllers, switches, valves, and so forth, may be present in various embodiments, such equipment is not shown in the figures for the sake of clarity.

The description can use the phrases "in some embodiments," "in various embodiments," "in an embodiment," "in at least one embodiment," or "in embodiments," which can each refer to one or more of the same or different embodiments. Furthermore, the terms "comprising," "including," "having," and the like, as used with respect to embodiments of the present disclosure are synonymous.

In this disclosure and the appended claims, unless otherwise indicated, all numbers expressing quantities, percentages or proportions, and other numerical values used in the specification and claims are to be understood as being modified in all instances by the term "about." The term "about" applies to all numeric values, whether or not explicitly indicated.

Ranges can be expressed in this disclosure as from about one particular value and to about another particular value. With these ranges, another embodiment is from the one particular value to the other particular value, along with all combinations within the range. When the range of values is described or referenced in this disclosure, the interval encompasses each intervening value between the upper limit and the lower limit, as well as the upper limit and the lower limit; and includes lesser ranges of the interval subject to any specific exclusion provided.

Ordinal numbers (such as "first," "second," "third," and so on), when used in this disclosure as an adjectives before a term, merely identify a particular component, feature, step, or combination of these unless expressly provided otherwise. At times, ordinal numbers may be used to distinguish a particular feature, component, or step from another feature, component, or step that is described by the same term or similar term. Unless expressly provided otherwise, ordinal numbers do not indicate any relationship, order, quality, ranking, importance, or characteristic between features, components, steps, or combinations of these. Moreover, ordinal numbers do not define a numerical limit to the features, components, steps, or combination they identify.

Where a method comprising two or more defined steps is recited or referenced in this disclosure, or the appended claims, the defined steps can be carried out in any order or simultaneously except where the context excludes that possibility.

Having an accurate view of the hydrocarbons produced from one or more wells enables operators to make decisions regarding the economic potential of the one or more wells, and the oil field more generally. Advantageously, the methods and apparatuses disclosed here are capable of providing near-instantaneous fluid measurements to support such decisions. Wells producing a significant water cut can be identified, and isolated if necessary, so that resources are conserved. Because the processes and devices can be automated, measurements can be carried out routinely with minimal labor costs and reduced potential for error. Moreover, the design of the methods and devices enables the use of materials that would otherwise be unsuitable because of corrosion. In an aspect, the processes and devices allow for the use of sensors or probes which would otherwise be unsuitable. The methods and devices can also be used to approximate actual properties of aqueous liquid phases from discrete samples of a multiphase fluid continuously. The methods and devices can also result in reduced fouling of sensors or probes, resulting in more accurate measurements and enabling the process to continue uninterrupted for greater periods of time. The data obtained using the processes and devices disclosed can be used to calibrate, optimize, or control a multiphase flow meter, for example, at a gas-oil separation plant.

Figure 1:
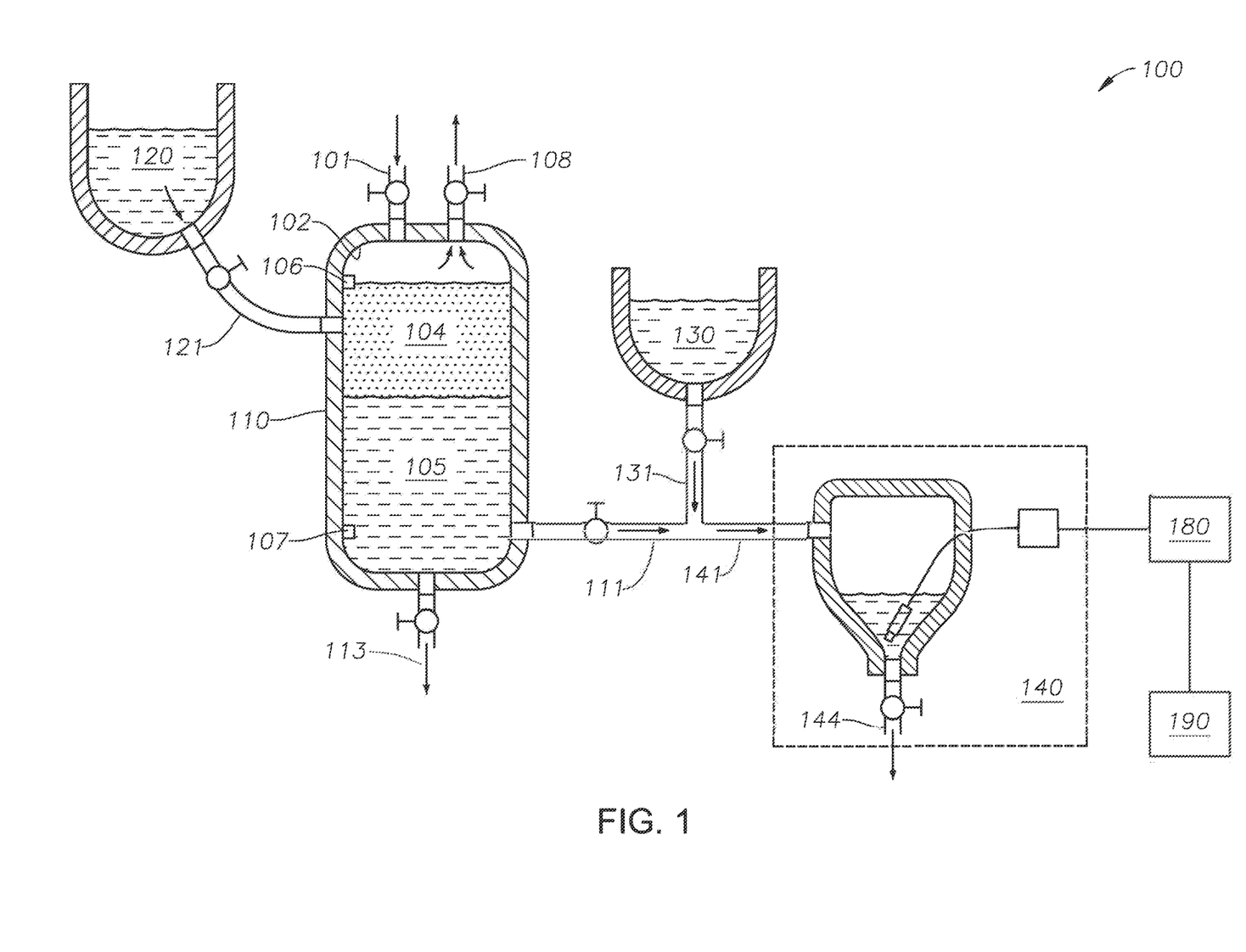
FIG. 1 is a schematic illustration of a process and device for separating, diluting, and analyzing an aqueous liquid phase sample from a discrete sample of a multiphase fluid mixture.

FIG. 1 is a schematic illustration of a process and device for separating and analyzing a multiphase fluid. In FIG. 1, the system 100 includes a separation vessel 110 having a first inner chamber 102. The separation vessel 110 has a first level indicator 106 and a second level indicator 107. The first level indicator 106 and second level indicator 107 can be used to control the flow of the multiphase fluid into and out of the separation vessel 110. For example, the first level indicator 106 can be configured to trigger flow of the multiphase fluid to stop when the first inner chamber 102 of the separation vessel 110 is full, and the second level indicator 107 can be configured to trigger filling of the first inner chamber 102 of the separation vessel 110 with the multiphase fluid after it has been emptied. The first level indicator 106 and second level indicator 107 can be any device (e.g., an optical sensor, radar sensor, window, float, etc.) suitable for indicating the level of liquid held in the first inner chamber 102 of the separation vessel 110. Though FIG. 1 shows two level indicators (i.e., first level indicator 106 and second level indicator 107), a person of ordinary skill will appreciate that some embodiments can use a single level indicator, and others may use more than two level indicators. For example, a window can be provided in the separation vessel 110 that extends in a vertical direction from top to bottom such that the liquid level can be observed at various points. In another example, a sensor can be provided at or near the top of the first inner chamber 102 to measure the distance between the sensor and the surface of the liquid contained in the separation vessel 110. In at least one embodiment, a separation vessel 110 can be manufactured from an at least partially translucent or transparent material such that the level of liquid inside the vessel can be determined by observation from outside the separation vessel 110. In at least one embodiment, the separation vessel 110 can be made of shatter-proof glass and can include markings for measuring the volume of liquid contained within. In at least one embodiment, the level indicator can be omitted.

A discrete sample of a multiphase fluid is delivered to separation vessel 110 by multiphase fluid stream 101. The multiphase fluid can be characterized as a fluid that includes a mixture of at least an aqueous liquid phase and a nonpolar liquid phase. In some embodiments, the multiphase fluid can include aqueous liquid droplets dispersed in the nonpolar liquid phase, nonpolar liquid droplets dispersed in the aqueous liquid phase, or both. The multiphase fluid can include an emulsion of aqueous liquid droplets emulsified in the nonpolar liquid phase, nonpolar liquid phase droplets emulsified in the aqueous liquid phase, or both. The aqueous liquid phase can include produced water from a hydrocarbon-bearing formation. The nonpolar liquid phase can include crude oil produced from a hydrocarbon-bearing formation. In one or more embodiments, the multiphase fluid includes a gas phase. The gas phase can include gases produced from a hydrocarbon-bearing formation, such as hydrocarbons, carbon oxides, hydrogen sulfide, mercaptans, etc. The gas phase can be dissolved in the liquid phases of the multiphase fluid when it is introduced to the separation vessel 110. In at least one embodiment, the multiphase fluid can be a fluid extracted from a hydrocarbon-bearing formation. In at least one embodiment, the multiphase fluid can be processed to remove dissolved gases. In some embodiments, the multiphase fluid can be collected in a test trap (e.g., a high pressure production trap or low pressure production trap), and then flown to the separation vessel 110. In at least one embodiment, the multiphase fluid can be provided from a high-pressure sample line.

As the first inner chamber of the separation vessel 110 is filled with the multiphase fluid, gases displaced by the multiphase fluid exit the separation vessel 110 in gas vent stream 108. The gas vent stream 108 can also be used to vent gases that come out of solution during or after filling the separation vessel 110. The gas that is vented from the separation vessel 110 through gas vent stream 108 can be measured using a flow meter (not shown).

A measured amount of demulsifier from a demulsifier source 120 is introduced to the separation vessel 110 by demulsifier stream 121 and is mixed with the multiphase fluid to obtain a demulsified multiphase fluid. The demulsifier source 120 can be any container or vessel (e.g., reservoir, tank, tube, injector, etc.) containing a demulsifier and that is suitable for storing the same. In some embodiments, the demulsifier can be mixed with the multiphase fluid before being introduced to the separation vessel 110. In some embodiments, the demulsifier can be actively mixed with the multiphase fluid using a mixer (not shown). The demulsifier can be any chemical, such as a surface-active agent, that facilitates the aggregation of dispersed droplets of the aqueous liquid phase or the nonpolar liquid phase. The type of demulsifier can be selected based on the type of crude oil and the amount of produced water that is typically produced. Conventional demulsifiers for breaking oil-water emulsions are known to one of ordinary skill, and are suitable for separating the multiphase fluid to obtain a demulsified multiphase fluid. Such demulsifiers can be obtained from vendors such as Nalco Water and ChampionX, 1 Ecolab Place, St. Paul, Minn. 55102-2233, and Baker Hughes Incorporated, P.O. Box 4740, Houston, Tex. 77210-4740. The amount of demulsifier that is used can be an amount sufficient to facilitate the aggregation of dispersed droplets of the aqueous liquid phase or nonpolar liquid phase such that the bulk aqueous liquid phase and nonpolar liquid phase are separated. Excess demulsifier, however, can slow separation of the multiphase fluid and produce very stable emulsions. According to at least one embodiment, the amount of demulsifier is sufficient to produce a concentration of 5-10 ppmv in the multiphase fluid. In FIG. 1, the multiphase fluid has been mixed with the demulsifier to obtain a separated nonpolar liquid phase 104 and a separated aqueous liquid phase 105. The multiphase fluid is allowed to separate for a period of time. In at least one embodiment, the period of time can be between about 1 minute and 24 hours, preferably between about 20 minutes and 12 hours, more preferably between about 1 and 5 hours, even more preferably between 2 and 3 hours. In at least one embodiment, the period of time can be about 2 hours.

After separating the aqueous liquid phase and the nonpolar liquid phase, at least a portion of the aqueous liquid phase is drawn from the separation vessel 110 and conducted by aqueous liquid phase stream 111. The separation vessel 110 can have an aqueous liquid phase outlet that is configured to draw the sample of the aqueous liquid phase. For example, the aqueous liquid phase outlet can be located in a portion of the separation vessel 110 where the aqueous liquid phase outlet is likely to accumulate. In many cases, the aqueous liquid phase will be denser than the nonpolar liquid phase and well settle beneath the nonpolar liquid phase. Therefore, the aqueous liquid phase outlet can be located in a lower portion of the separation vessel 110. In at least one embodiment, the aqueous liquid phase outlet can be the opening of a tube, pipe, or conduit that is located in a portion of the separation vessel 110 where the aqueous liquid phase is likely to accumulate after separating. The aqueous liquid phase sample can be drawn by any means suitable for drawing a liquid such as siphoning, pouring, pumping, etc.

Fresh water from fresh water reservoir 130 is delivered by freshwater stream 131 to aqueous liquid phase stream 111 and is mixed with the aqueous liquid phase sample to obtain a diluted aqueous liquid phase sample. The mixing can be achieved using any method known to one of ordinary skill, such as by active mechanical mixing, or injecting one stream into the other. According to at least one embodiment, the aqueous liquid phase stream 111 and the freshwater stream 131 can be introduced to the water analysis unit 140 separately and mixed in the water analysis unit 140. The amount (i.e., mass, volume, or both) of the aqueous liquid phase that is mixed with the fresh water can be measured using known methods and instruments, and the measurement can be sent to processing unit 180. Likewise, the amount (i.e., volume, mass, or both) of fresh water that is used to dilute the aqueous liquid phase sample can be measured using known methods and instruments, and the measurement sent to processing unit 180. The amount of fresh water used to dilute the aqueous liquid phase sample can be predetermined based on conditions, characterization of produced water, application requirements, or a combination of the same. In at least one embodiment, the amount of aqueous liquid phase sample and the amount of fresh water used to dilute the aqueous liquid phase sample can be predetermined. In at least one embodiment, the fresh water can be deionized water. In at least one embodiment, the ratio of fresh water to aqueous liquid phase sample in the diluted aqueous liquid phase sample can be between about 50:1 and 1:1, preferably between about 30:1 and 1:1, more preferably between about 10:1 and 15:1. The diluted aqueous liquid phase sample is conducted by diluted aqueous liquid phase sample stream 141 to water analysis unit 140.

Diluting the aqueous liquid phase sample with fresh water ensures that the capacity of the probes is not overloaded and increases the volume of relatively small samples so that they can be analyzed. This step can also reduce the corrosive potential of the aqueous liquid sample, allowing system components to be manufactured from materials which might otherwise be unsuitable.

Figure 2:
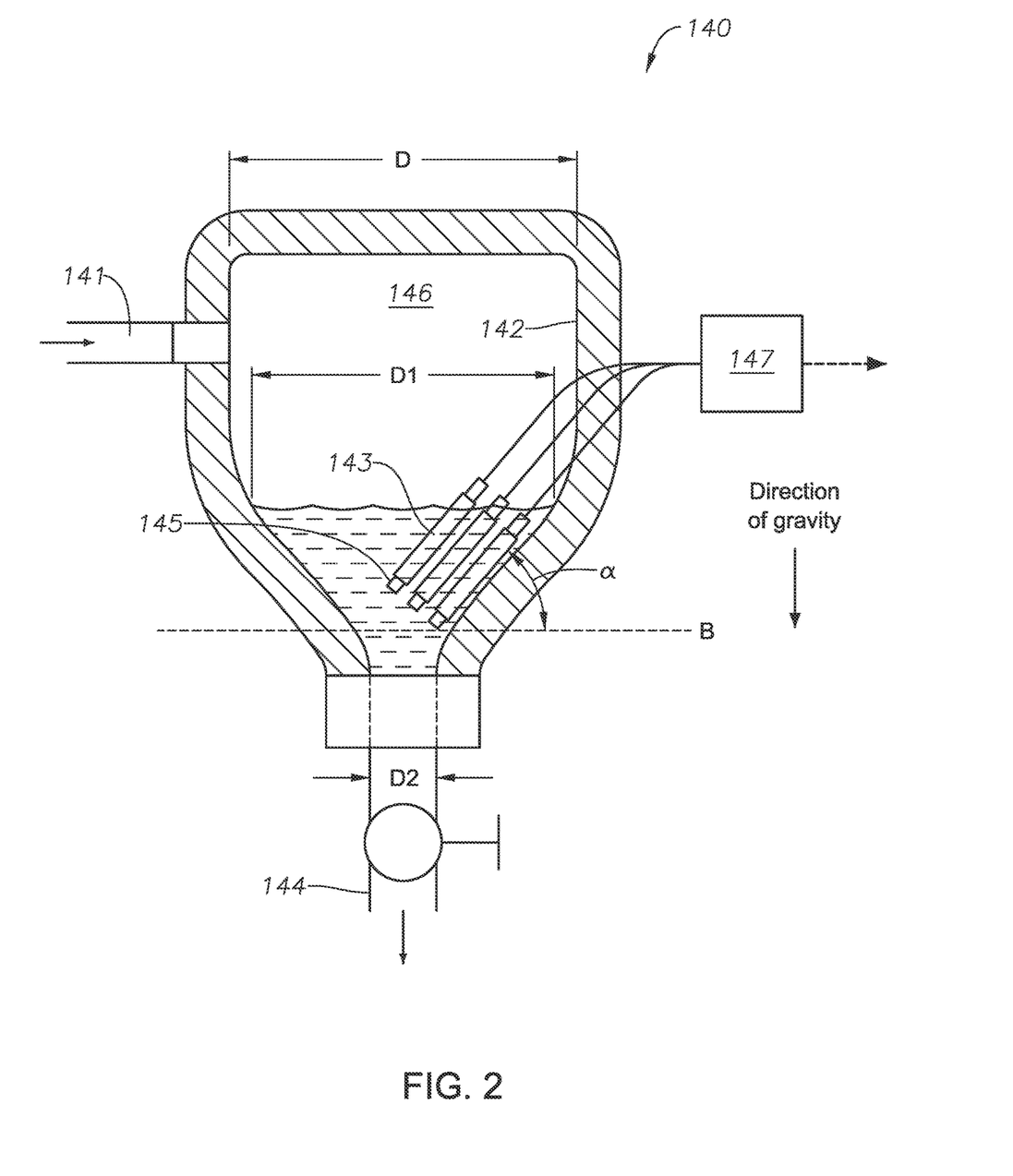
FIG. 2 is a schematic illustration of a water analysis unit for analyzing a diluted aqueous liquid phase sample from a discrete sample of a multiphase fluid mixture.

Referring now to FIG. 2, which shows a schematic illustration of a water analysis unit 140 for analyzing a diluted aqueous liquid phase sample. The water analysis unit 140 includes at least one analytical cell 146. As shown in FIG. 2, the analytical cell can have a second inner chamber 142 defining a space having a shape that narrows toward a minimum point (e.g., a funnel shape, rounded bottom, etc.) to provide a suitable depth of the diluted aqueous liquid phase sample so that membrane-coated sensor tips 145 of one or more probes 143 can be immersed in the diluted aqueous liquid phase sample. The analytical cell 146 can have a cell diameter D representing the average distance across an inner cross section of the analytical cell taken perpendicular to the direction of gravity. The portion of the analytical cell that is wetted by the diluted aqueous liquid phase sample when present inside the analytical cell can have a cell diameter D that decreases in the downward direction (i.e., the direction of gravity). For example, upper cell diameter D1 represents the diameter measured at the meniscus of the diluted aqueous liquid phase sample after the analytical cell has been filled, and lower cell diameter D2 represents the diameter measured at the lowest portion of the analytical cell that is wetted by the diluted aqueous liquid phase sample. As shown in FIG. 2, the cell diameter between the upper cell diameter D1 and the lower cell diameter D2 can decrease in the direction of gravity so that upper cell diameter D1 is greater than lower cell diameter D2. According to at least one embodiment, D1 and D2 have a ratio between about 21:20 and 100:1, preferably between about 11:10 and 80:1, more preferably between about 5:4 and 50:1, even more preferably between about 3:2 and 30:1. An advantage of the analytical cell shown in FIG. 2 over an analytical cell having a uniform narrow diameter is that the sensors 143 can be located proximally instead of being spaced vertically.

In addition to improving the depth of the diluted aqueous liquid phase sample, the shape of the analytical cell 146 can improve the accuracy of subsequent measurements. It has been found that subsequent diluted aqueous liquid phase samples can be contaminated by liquid that remains in the analytical cell 146 if it does not have a shape that funnels liquid toward an outlet. By designing the analytical cell 146 so that it has the described shape, the analytical cell 146 can be more completely emptied using only the force of gravity.

The analytical cell 146 has one or more probes 143 having one or more membrane-coated sensor tips 145. The one or more membrane-coated sensor tips 145 are positioned in the analytical cell 146 such that they are immersed in the diluted aqueous liquid phase sample after it has been introduced to the analytical cell 146. The one or more probes 143 can include ion-selective electrodes for measuring one or more properties (e.g., total dissolved solids (TDS), salinity, pH conductivity, sodium concentration, chloride concentration, sulfate concentration, carbonate concentration, nitrate concentration, etc., or any combination of the same) of the diluted aqueous liquid phase. The number and type of probe used can be selected based on the type of produced water and the application requirements. A nonlimiting example of a suitable sensor can be an ion-selective electrode, such as those available commercially and known to one of ordinary skill. Preferably, the sensor can be an ion-selective electrode having a stainless steel body and a sensing area that is covered with a layer of an ion-exchange polymer to protect the sensor from corrosion.

In at least one embodiment, the one or more probes 143 can have an oblong shape with the membrane-coated sensor tip 145 located at an end. The one or more probes 143 can be oriented in a fixed position with the membrane-coated sensor tip 145 in the downward direction so that there exists an acute angle a measured from the one or more probes 143 to a horizontal plane B. Orienting the one or more probes 143 in this manner has the effect of allowing multiple probes 143 to be positioned so that the membrane-coated sensor tips 145 of multiple probes 143 can be positioned and immersed in diluted aqueous liquid phase samples having a volume that is insufficient to fill the analytical cell 146. Compared with probes oriented in a vertical or horizontal direction, orienting the one or more probes 143 at an acute angle also has the effect of reducing the accumulation of oil droplets near the sensor tip. The acute angle a can be between about 80° and 10°, preferably between about 60° and 30°. In at least one embodiment, the acute angle a can be 45°.

The membrane-coated sensor tip 145 can include a sensor tip having a membrane coating that includes a polar material. Even when present in extremely limited quantities, oil in the diluted aqueous liquid phase sample can foul the sensor tip of a probe. The polar material coating can help to prevent the accumulation of oil droplets near the sensor tip and fouling of the sensor tip. The polar material can be any material suitable for coating a sensor tip for use in an aqueous environment, and that is sufficiently permeable to allow the diluted aqueous liquid phase sample to contact the sensor tip. For example, the polar material can include a polymer such as polyvinyl acetate, polyimide, polybenzimidazole, polyacrylonitrile, polyethersulfone, sulfonated tetrafluoroethylene-based fluoropolymer-copolymer, or similar materials, and combinations of the same. In at least one embodiment, the polar material coating can have a thickness between about 0.003 inches (in) and 0.01 in, preferably between about 0.004 in and 0.006 in. According to at least one embodiment, the polar material is applied directly to the surface of the sensor tip. In at least one embodiment, the sensor tip can be completely enveloped by the polar material coating so that no surface of the sensor tip is directly exposed to the diluted aqueous liquid phase sample when present.

The analytical cell 146 can be configured to receive the diluted aqueous liquid phase sample from diluted aqueous liquid phase stream 141 and measure one or more physical or chemical properties of the diluted aqueous liquid phase sample using the one or more probes 143. In at least one embodiment, the diluted aqueous liquid phase can be held in contact with the one or more membrane-coated sensor tips 145 in the analytical cell 146 for a period of time so that conditions in the analytical cell 146 can stabilize and a steady reading can be obtained. In at least one embodiment, the period of time is between about 30 seconds and 1 hour, preferably between about 1 minute and about 20 minutes, more preferably between about 2 minutes and 15 minutes, even more preferably between about 3 minutes and 10 minutes.

The water analysis unit 140 can include a control box 147 that is configured to receive readings from the one or more probes 143, convert the readings to diluted aqueous liquid phase data in a digital form, and electronically send the diluted aqueous liquid phase data to processing unit 180. The analytical cell 146 can be emptied by way of water analysis effluent 144. After emptying, the analytical cell 146 can be flushed with fresh water to prepare it for subsequent readings. The steps of filling, taking of measurements, emptying, and flushing of the analytical cell 146 can each be automated. In at least one embodiment, the process is automated using a closed loop controller.

Referring again to FIG. 1, Diluted aqueous liquid phase sample data from the one or more probes 143 is sent to processing unit 180 where it is recorded. The processing unit 180 can be configured to calculate approximate corresponding values from the diluted aqueous liquid phase sample data for the nondiluted aqueous liquid phase sample by adjusting the diluted aqueous liquid phase sample data to account for the amount of dilution. For example, if the property of the aqueous liquid phase can be approximated using a linear equation, an approximate aqueous liquid phase property data value for the nondiluted aqueous liquid phase sample can be calculated using Eqn. 1.

$$Y = X_1 + \frac{V_f}{V_i}(X_1 - X_0)$$ Eqn. 1

Where $X_0$ is the value of the observed property of the fresh water, $X_1$ is the value of the observed property of the diluted aqueous liquid phase sample, $V_f$ is the volume of fresh water, $V_i$ is the volume of the portion of the aqueous liquid phase that is drawn from the separation vessel 110 before it is diluted, and Y represents the approximate value of the corresponding property in the nondiluted aqueous liquid phase sample. The processing unit 180 can also be configured to adjust the calculated data to account for properties of the fresh water that is used to dilute the aqueous liquid phase sample. For example, if the property to be approximated is the concentration of a solute, the processing unit 180 can be configured to adjust the calculated data to account for a known preexisting concentration of the solute in the fresh water that is used to dilute the aqueous liquid phase sample. In at least one embodiment, the processing unit 180 can be a distributed control system.

The approximate value or values calculated by the processing unit 180 can be used to calibrate, optimize, or control a multiphase flow meter 190. In at least one embodiment, the multiphase flow meter 190 is used to measure the flow of oil and produced water at a gas-oil separation plant. In at least one embodiment, the multiphase flow meter 190 is used to measure the flow of oil and produced water at a well. The system 100 can be used to analyze discrete multiphase fluid samples from individual wells, allowing less-productive wells to be identified. In at least one embodiment, the period of time measured from the introduction of the discrete sample of the multiphase fluid to the first inner chamber of the separation vessel 110 to the calibration of the multiphase flow meter can be between about 5 minutes and 24 hours, alternatively between about 5 minutes and 10 hours, preferably between 5 minutes and 6 hours, more preferably between about 30 minutes and 3 hours.

After the diluted aqueous liquid phase sample has been analyzed, it is removed from the water analysis unit 140 in water analysis effluent 144. Fresh water from fresh water reservoir 130 can be used to flush the water analysis unit and prepare it to receive subsequent samples. The first inner chamber of the separation vessel 110 is emptied through separation vessel effluent 113. In at least one embodiment, the first inner chamber of the separation vessel 110 can be flushed with fresh water in preparation for receiving the next sample. The process can then be repeated with a new discrete sample of the multiphase fluid. The process can be automated so that discrete samples of the multiphase fluid are continuously measured, recorded, and used to calibrate, optimize, or control the multiphase flow meter with minimal or no supervision. Automation of the process allows data to be fed directly to a controller so that the process of well monitory can be streamlined and the potential for error reduced.

EXAMPLES

The following examples are included to demonstrate embodiments of the disclosure, and should be considered nonlimiting. The examples which follow represent techniques, systems, compositions, and apparatuses discovered to function well in the practice of the disclosure, and thus can be considered to constitute modes for its practice. However, changes can be made to the embodiments disclosed in the examples without departing from the spirit and scope of the disclosure.

Example 1

Laboratory-Scale Experiment Using a System for Separating a Multiphase Fluid, and Diluting and Analyzing the Aqueous Liquid Phase A laboratory-scale experiment was carried out using a system for separating a multiphase fluid, and diluting and analyzing the aqueous liquid phase similar to the system and process shown in FIG. 1 and FIG. 2. Multiple multiphase samples having varying ratios of oil to produced water between 60/40 and 90/10 by volume were tested. The samples were taken from various gas-oil separation plants. The system included a separation vessel made of shatterproof glass. The system was configured to fill the separation vessel with a multiphase fluid from a gas-oil separation plant, introduce a demulsifier, and allow separation of the aqueous liquid phase and the nonpolar liquid phase to be carried out for a period of about 2 hours. The aqueous liquid phase and the nonpolar liquid phase separated after about 2 hours, with the aqueous liquid phase settling underneath the nonpolar liquid phase.

A measured amount of the aqueous liquid phase was automatically drawn from the lower portion of the first inner chamber of the separation vessel, diluted with a measured amount of fresh water including deionized water from a fresh water reservoir, and sent to a water analysis unit. The water analysis unit included an analytical cell having ion-selective electrodes for measuring conductivity, chloride, and total dissolved solids (TDS). The ion-selective electrodes had membrane-coated sensor tips that were coated with a sulfonated tetrafluoroethylene-based fluoropolymer-copolymer, available under the brand name Nafion™ from The Chemours Company Corp., 1209 Orange St., Wilmington, Del. 19801. The diluted sample was allowed to settle in the analytical cell for 10 minutes, so that readings from the probes were stable. Readings from the probes were sent to a control box, which produced digital data that were sent to a computer. The water analysis unit was configured to carry out the analysis automatically. Approximate values of the same properties for the nondiluted aqueous liquid phase were calculated by accounting for the degree of dilution, and the calculated data were then recorded.

After the diluted aqueous liquid phase sample was analyzed in the analytical cell of the water analysis unit, the flow cells in the water analysis unit and the first inner chamber of the separation vessel were flushed with deionized water, and the process was repeated with a subsequent discrete multiphase fluid sample. The data obtained using the system and process are shown in Table 1.

TABLE 1

Physical properties of nondiluted aqueous liquid phase samples from various multiphase fluids from various gas-oil separation plants. The data were calculated using observed data from diluted aqueous liquid phase samples.

| Sample | Oil/Water (vol/vol) | Chloride (ppm) | Conductivity (µS/cm) | TDS (ppm) |
|---|---|---|---|---|
| 1 | 80/20 | 32,566 | 12,900 | 14,320 |
| 2 | 90/10 | 29,878 | 10,570 | 12,400 |
| 3 | 95/5 | 36,216 | 13,380 | 17,730 |
| 4 | 65/35 | 28,890 | 10,075 | 11,216 |
| 5 | 60/40 | 37,230 | 14,580 | 15,908 |
| 6 | 70/30 | 32,138 | 12,780 | 13,250 |
| 7 | 80/20 | 35,007 | 13,745 | 15,980 |
| 8 | 90/10 | 29,780 | 10,735 | 12,656 |
| 9 | 90/10 | 34,875 | 13,445 | 15,678 |

The calculated approximate values shown in Table 1 were confirmed to be within plus or minus 5% of actual values as determined using conventional laboratory techniques.

The drawings provide an illustration of certain embodiments. Other embodiments can be used, and logical changes can be made without departing from the scope of this disclosure. This disclosure is intended to disclose certain embodiments with the understanding that many other undisclosed changes and modifications can fall within the spirit and scope of the disclosure. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal language of the claims.

Unless otherwise defined, all technical and scientific terms used in this specification and the appended claims have the same meanings as commonly understood by one of ordinary skill in the relevant art.

We claim:

1. A device for separating and analyzing an aqueous liquid phase from a multiphase fluid produced from a hydrocarbon-bearing formation, the device comprising:
   a separation vessel having a first inner chamber defined in the separation vessel for containing a discrete sample of the multiphase fluid;
   a multiphase fluid inlet in the separation vessel to allow the discrete sample of the multiphase fluid to flow into the first inner chamber of the separation vessel;
   an aqueous liquid phase outlet in the separation vessel that is configured to draw a measured sample of an aqueous liquid phase from within the inner chamber, and an aqueous liquid phase stream that is configured to conduct the sample of the aqueous liquid phase;
   a demulsifier source in fluid communication with the separation vessel and configured to introduce a demulsifier to the first inner chamber of the separation vessel;
   a fresh water source that is in fluid communication with the aqueous liquid phase stream and configured to introduce a measured amount of fresh water to the measured sample of the aqueous liquid phase to obtain a diluted aqueous liquid phase sample;
   a water analysis unit that is in fluid communication with the aqueous liquid phase stream and that is configured to receive the diluted aqueous liquid phase sample and analyze the same, the water analysis unit comprising an analytical cell having a second inner chamber and at least one probe, the at least one probe having a membrane-coated sensor tip having a membrane coating that comprises a polar material, the at least one probe being configured to measure a property of the diluted aqueous liquid phase sample to obtain diluted aqueous liquid phase sample data;
   a processing unit that is configured to receive the diluted aqueous liquid phase sample data and calculate an approximate aqueous liquid phase data by accounting for the measured amount of fresh water used to dilute the measured sample of the aqueous liquid phase.

2. The device of claim 1, wherein the at least one probe is configured to measure a property selected from the group consisting of total dissolved solids (TDS), salinity, pH, conductivity, sodium concentration, chloride concentration, sulfate concentration, carbonate concentration, nitrate concentration, and any combination of the same.

3. The device of claim 1, wherein the at least one probe comprises an ion-selective electrode.

4. The device of claim 1, wherein the at least one probe is oriented in a fixed position in the second inner chamber with the membrane-coated sensor tip in a downward direction so that there exists an acute angle measured from the at least one probe to a horizontal plane.

5. The device of claim 4, wherein the acute angle is between 10 and 80 degrees.

6. The device of claim 1, wherein the polar material comprises a material selected from the group consisting of polyvinyl acetate, polyimide, polybenzimidazole, polyacrylonitrile, polyethersulfone, and combinations of the same.

7. The device of claim 1, wherein the second inner chamber defines a space having a shape that funnels liquid toward an outlet.

8. The device of claim 1, wherein the processing unit is configured to calculate the approximate aqueous liquid phase data by accounting for the measured amount of fresh water used to dilute the measured sample of the aqueous liquid phase and a corresponding property of the fresh water.

9. The device of claim 1, wherein the analytical cell comprises a closed loop controller for emptying and filling the analytical cell.

10. The device of claim 1, further comprising a control box configured to receive a reading from the at least one probe, convert the reading to the diluted aqueous liquid phase data in a digital form, and electronically send the diluted aqueous liquid phase data to the processing unit.

11. A method for obtaining an approximate aqueous liquid phase property data from a multiphase fluid that is produced from a hydrocarbon-bearing formation and using the approximate aqueous liquid phase property data to calibrate a multiphase flow meter, the method comprising the steps of:
introducing a discrete sample of the multiphase fluid to a separation vessel;
introducing and mixing a demulsifier with the discrete sample of the multiphase fluid in the separation vessel;
allowing the multiphase fluid to separate for a first period of time into separate liquid phases comprising an aqueous liquid phase and a nonpolar liquid phase;
drawing a measured sample of the aqueous liquid phase from the separation vessel, and diluting it with a measured amount of fresh water to obtain a diluted aqueous liquid phase sample;
analyzing the diluted aqueous liquid phase sample in a water analysis unit to measure a property of the diluted aqueous liquid phase sample and obtain diluted aqueous liquid phase sample data by introducing the diluted aqueous liquid phase sample to an analytical cell having at least one probe configured to measure a property of the diluted aqueous liquid phase sample, allowing the diluted aqueous liquid phase sample to remain in contact with the at least one probe for a second period of time, using the at least one probe to observe the property and obtain the diluted aqueous liquid phase sample data;
calculating the approximate aqueous liquid phase property data by adjusting the diluted aqueous liquid phase sample data to account for the measured amount of fresh water used to dilute the measured sample of the aqueous liquid phase; and
using the approximate aqueous liquid phase property to calibrate the multiphase flow meter.

12. The method of claim 11, wherein the property of the diluted aqueous liquid phase sample is selected from the group consisting of total dissolved solids (TDS), salinity, pH, conductivity, sodium concentration, chloride concentration, sulfate concentration, carbonate concentration, nitrate concentration, and any combination of the same.

13. The method of claim 11, wherein the step of analyzing the diluted aqueous liquid phase sample in a water analysis unit is carried out using a probe comprising an ion-selective electrode.

14. The method of claim 11, wherein the first period of time is between 20 minutes and 24 hours.

15. The method of claim 11, wherein the second period of time is between 30 seconds and 1 hour.

16. The method of claim 11, further comprising flushing the analytical cell with fresh water after measuring the diluted aqueous liquid phase sample.

17. The method of claim 11, further comprising emptying the first inner chamber of the separation vessel and flushing and flushing it with fresh water.

18. The method of claim 17, wherein the water analysis unit and the first inner chamber of the separation vessel are emptied and the steps are repeated continuously.

19. The method of claim 11, the steps are carried out over a third period of time that is between 5 minutes and 6 hours.

* * * * *